(12) United States Patent
Matsumoto et al.

(10) Patent No.: US 10,163,202 B2
(45) Date of Patent: Dec. 25, 2018

(54) AUTOMATIC BLOOD-SAMPLING TUBE PREPARATION DEVICE

(75) Inventors: Toshikazu Matsumoto, Yokohama (JP); Yoshimi Hirasawa, Yokohama (JP); Yasushi Nakano, Yokohama (JP); Yusuke Wada, Kawasaki (JP); Ichiro Nakamura, Kawasaki (JP)

(73) Assignee: TECHNO MEDICA CO., LTD., Yokohama-shi (JP)

( * ) Notice: Subject to any disclaimer, the term of this patent is extended or adjusted under 35 U.S.C. 154(b) by 117 days.

(21) Appl. No.: 14/117,650

(22) PCT Filed: May 18, 2011

(86) PCT No.: PCT/JP2011/061375
§ 371 (c)(1),
(2), (4) Date: Jan. 16, 2014

(87) PCT Pub. No.: WO2012/157085
PCT Pub. Date: Nov. 22, 2012

(65) Prior Publication Data
US 2014/0125797 A1    May 8, 2014

(51) Int. Cl.
*H04N 7/18* (2006.01)
*G06T 7/00* (2017.01)
(Continued)

(52) U.S. Cl.
CPC ............ *G06T 7/0012* (2013.01); *A61B 5/153* (2013.01); *A61B 5/15077* (2013.01);
(Continued)

(58) Field of Classification Search
CPC ......... G01N 35/04; G01N 2035/00861; G01N 2035/0406; G01N 2035/0465
(Continued)

(56) References Cited

U.S. PATENT DOCUMENTS

| 2004/0005245 A1* | 1/2004 | Watson | B65G 47/1471 422/65 |
| 2004/0159589 A1* | 8/2004 | Matsumoto | G01N 35/04 209/546 |
| 2010/0066996 A1* | 3/2010 | Kosaka | G01F 23/292 356/39 |

FOREIGN PATENT DOCUMENTS

| JP | 2005-065990 A | 3/2005 |
| JP | 2005-067660 A | 3/2005 |

(Continued)

OTHER PUBLICATIONS

International Search Report (in Japanese with English translation) for PCT/JP2011/061375, dated Aug. 30, 2011; ISA/JP.

*Primary Examiner* — Frederick D Bailey
*Assistant Examiner* — Masum Billah
(74) *Attorney, Agent, or Firm* — Harness, Dickey & Pierce, P.L.C.

(57) ABSTRACT

The present invention provides an automatic blood-sampling tube preparation device which can detect the presence of the proper or improper blood-sampling tube by selectively taking out a blood-sampling tube and transferring the blood-sampling tube to a label pasting position, printing information of the patient on a label, pasting the printed label on the blood-sampling tube positioned in the label pasting position, and collecting the label pasted blood-sampling tubes in the container for each patient. The device also includes photographing means for photographing an appearance of the blood-sampling tube taken out from the blood-sampling tube containing section and a control means arranged to have a threshold with respect to at least one characteristic information previously extracted from an appearance of a blood-sampling tube, to extract the characteristic information from the appearance image photo- (Continued)

graphed to judge whether the blood-sampling tube corresponds to the instruction information from the doctor.

10 Claims, 7 Drawing Sheets

(51) Int. Cl.
    *A61B 5/15*     (2006.01)
    *A61B 5/153*     (2006.01)
    *G01N 35/00*     (2006.01)
    *B65C 3/12*     (2006.01)
    *G06Q 50/22*     (2018.01)
    *B01L 3/00*     (2006.01)
    *A61B 5/154*     (2006.01)
    *B65C 9/00*     (2006.01)

(52) U.S. Cl.
    CPC .. *A61B 5/150274* (2013.01); *A61B 5/150786* (2013.01); *B01L 3/5453* (2013.01); *B65C 3/12* (2013.01); *G01N 35/00623* (2013.01); *G06Q 50/22* (2013.01); *A61B 5/15003* (2013.01); *A61B 5/154* (2013.01); *A61B 5/150259* (2013.01); *B01L 2200/143* (2013.01); *B01L 2300/021* (2013.01); *B65C 2009/0003* (2013.01); *G01N 2035/00752* (2013.01); *G01N 2035/00801* (2013.01); *G01N 2035/00861* (2013.01)

(58) Field of Classification Search
    USPC .............................. 348/129; 209/546; 221/92
    See application file for complete search history.

(56) References Cited

FOREIGN PATENT DOCUMENTS

| | | | | |
|---|---|---|---|---|
| JP | 2005121558 | A | * | 5/2005 |
| JP | 2009-077795 | A | | 4/2009 |
| JP | 2009077795 | A | * | 4/2009 |
| JP | 2010-110499 | A | | 5/2010 |

* cited by examiner

BLOOD-SAMPLING TUBE a   TUBE LENGTH: 100mm TUBE DIAMETER: 15.6m

BLOOD-SAMPLING TUBE b   TUBE LENGTH: 100mm TUBE DIAMETER: 13.2mm

BLOOD-SAMPLING TUBE c   TUBE LENGTH: 78mm TUBE DIAMETER: 15.6m

BLOOD-SAMPLING TUBE d   TUBE LENGTH: 78mm TUBE DIAMETER: 13.2mm

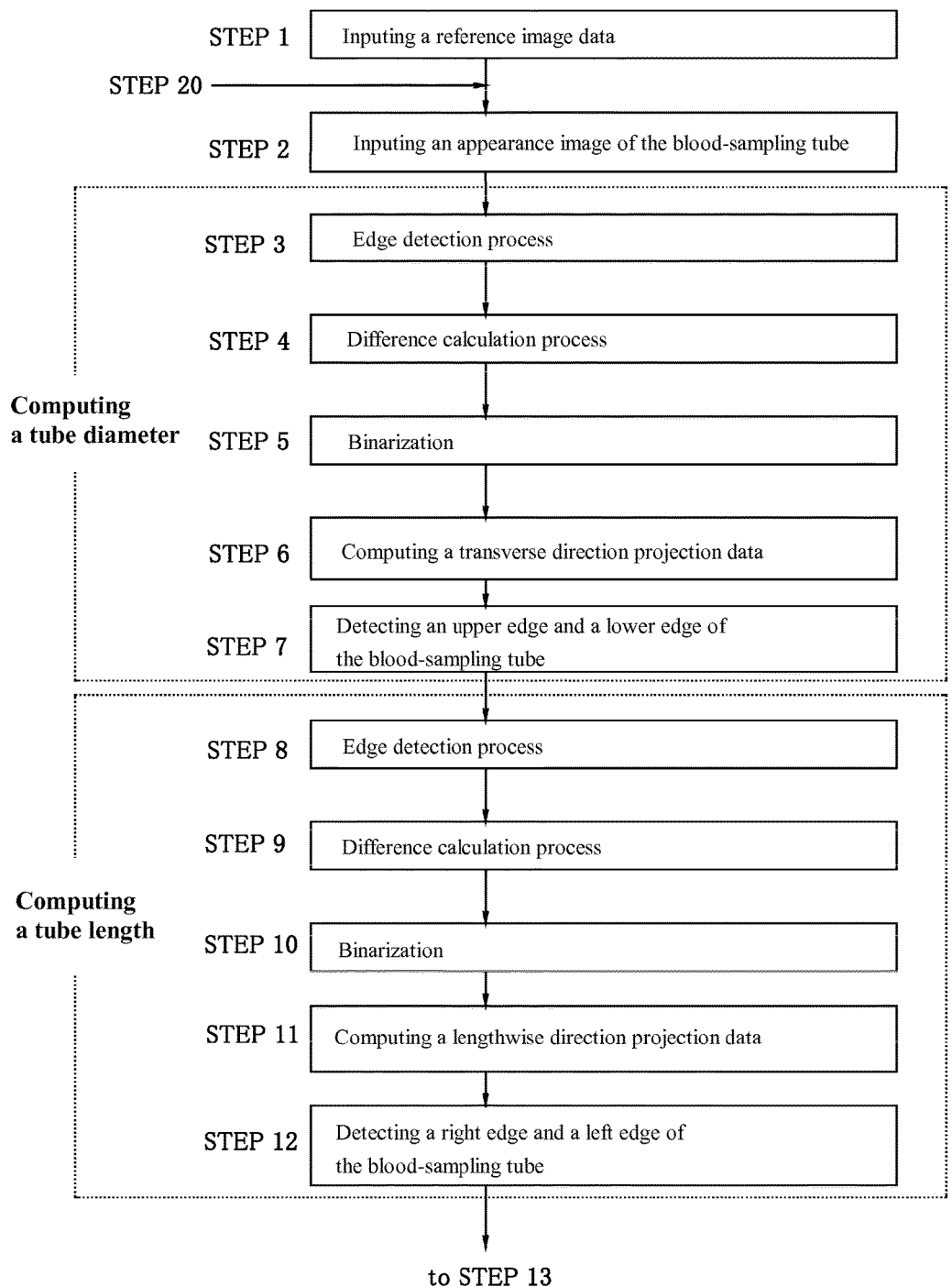

AUTOMATIC BLOOD-SAMPLING TUBE PREPARATION DEVICE

FIELD OF THE INVENTION

The present invention relates to the improvement of an automatic blood-sampling tube preparation device for preparing automatically one or more blood-sampling tubes that are used for blood sampling.

BACKGROUND OF THE INVENTION

Conventionally, in order to automatically prepare one or more blood-sampling tubes for every patient before sampling blood, an automatic blood-sampling tube preparation device has already been proposed. The automatic blood-sampling tube preparation device stores the blood-sampling tubes of a plurality of kinds in separate blood-sampling tube containing cases for each kind. The preparation device, based on information related to one patient, automatically selects a blood-sampling tube required to an examination for the patient, takes out the selected blood-sampling tube from the corresponding blood-sampling tube containing case, prints patient information such as a patient ID or examination information on a label to make an identification label, automatically pastes the identification label on an outer surface of the taken-out blood-sampling tube, and then collects one or more blood-sampling tubes, each having the identification label pasted for each patient, into a tray or a bag (Japanese Patent Kokai No. 2005-65990A).

In the above-mentioned automatic blood-sampling tube preparation device, one or more information are previously memorized, which associate the blood-sampling tube containing case with the kind of blood-sampling tube to be stored in it. Based on said memorized information and said information related to one patient, the blood-sampling tube required to the examination for the patient is selected and picked up from the containing case, and the label with the patient information or the examination information printed is pasted on the surface of the selected blood-sampling tube.

Problem(s) to be Solved by the Invention

When a worker puts or adds one or more blood sampling tubes into a blood sampling tube containing case, unless the worker makes a mistake to put the blood-sampling tube into the wrong containing case, the automatic blood sampling tube preparation device never take out the wrong blood-sampling tube.

However, since a worker i.e. a human does the work which puts one or more blood sampling tubes into a blood sampling tube containing section, it is impossible to completely eliminate a possibility of being putting the blood sampling tubes into the wrong blood sampling tube containing section.

If the worker puts one or more blood-sampling tubes into the wrong blood-sampling tube containing case, the preparation device will pick up the wrong blood-sampling tube not required to the examination of the patient and paste the label having the information related to the patient on said wrong blood-sampling tube. As a result, it is necessary to carry out re-pasting the label on a correct blood-sampling tube or discarding the wrong blood-sampling tube.

As mentioned above, if said mistake is discovered immediately, it may carry out re-pasting the label or discarding the wrong blood-sampling tube. However, if the wrong blood-sampling tube is used to sampling the blood from the patient, it must re-sample the blood from the patient and re-examine the blood, so that the problem becomes serious.

An object of the present invention is to provide an automatic blood-sampling tube preparation device which can solve the above-mentioned conventional problem and detect the mistake in the kind of blood-sampling tube.

Means for Solving the Problem

In order to achieve the above mentioned object, an automatic blood-sampling tube preparation device according to the present invention comprising at least two blood-sampling tube containing sections, each section being intended to contain blood-sampling tubes of a same type, a transfer means for selectively taking out a blood-sampling tube required to an examination of a patient according to an instruction information indicated by a doctor from the blood-sampling tube containing section and transferring the taken-out blood-sampling tube to a label pasting position, a label printing and pasting means for printing an information of the patient on a label and pasting the printed label on the blood-sampling tube positioned in the label pasting position, and a control means for controlling operations of each means characterized in that the automatic blood-sampling tube preparation device further comprises a photographing means for photographing an appearance of the blood-sampling tube taken out from the blood-sampling tube containing section, and said control means is arranged to have a threshold with respect to at least one characteristic information previously extracted from an appearance of a blood-sampling tube, to extract the characteristic information from the appearance image photographed by the photographing means, to specify the type of the blood-sampling tube taken out from the blood-sampling tube containing section on the basis of the threshold and the extracted characteristic information, and to judge whether the blood-sampling tube corresponds to the instruction information from the doctor.

Specifically, said characteristic information may include at least one of a tube diameter, a tube length, an existence of a cap, a cap diameter, a cap length, a cap color, an existence of a medical fluid inside a tube, and an existence of a label on a tube surface.

Also, said photographing means may be arranged upstream of the label printing and pasting means in the transporting direction of the blood-sampling tube.

Further, the control means may stop the transfer means if the blood-sampling tube taken out from the blood-sampling tube containing section is incorrect.

Furthermore, the automatic blood-sampling tube preparation device may be provided with an output means for outputting the judgment result by the control means to a user, and said control means may output the judgment result via the output means by using an image and/or a sound if the blood-sampling tube taken out from the blood-sampling tube containing section is incorrect.

Also, the automatic blood-sampling tube preparation device further may be provided with an input means by which a user inputs a user judgment result, the control means may output the judgment result via the output means by using the image and/or the sound if the blood-sampling tube taken out from the blood-sampling tube containing section is incorrect, and then the control means may receive as the final judgment result the user judgment result judged by the user on the basis of the outputted judgment result via the input means to control each means on the basis of the final judgment result. Specifically, when the control means judges that the taken-out blood-sampling tube is incorrect, a user checks visually the blood-sampling tube in question or the image thereof photographed by the photographing means, judges whether the blood-sampling tube is correct, and inputs the user judgment result via the input means.

Also, when the control means judges that the taken-out blood-sampling tube is incorrect, said control means controls the label printing and pasting means so as to attach a mark which indicates that the blood-sampling tube is incorrect. Specifically, for example, when the control means judges that taken-out blood-sampling tube is incorrect, the control means controls the label printing and pasting means so as to make an error label and paste it on the blood-sampling tube in question.

SUMMARY OF THE INVENTION

An automatic blood-sampling tube preparation device according to the present invention comprising at least two blood-sampling tube containing sections, each of which is intended to contain blood-sampling tubes of a same type, a transfer means for selectively taking out a blood-sampling tube required to an examination of a patient according to an instruction information indicated by a doctor from the blood-sampling tube containing section and transferring the taken-out blood-sampling tube to a label pasting position, a label printing and pasting means for printing an information of the patient on a label and pasting the printed label on the blood-sampling tube positioned in the label pasting position, and a control means for controlling operations of each means characterized in that the automatic blood-sampling tube preparation device further comprises a photographing means for photographing an appearance of the blood-sampling tube taken out from the blood-sampling tube containing section, and said control means is intended to have a threshold with respect to at least one characteristic information previously extracted from an appearance of a blood-sampling tube, to extract the characteristic information from the appearance image photographed by the photographing means, to specify the type of the blood-sampling tube taken out from the blood-sampling tube containing section on the basis of the threshold and the extracted characteristic information, and to judge whether the blood-sampling tube corresponds to the instruction information from the doctor.

Therefore, if blood-sampling tubes are contained in an incorrect containing section or an incorrect stock section, the automatic blood-sampling tube preparation device may automatically detect that the type of the blood-sampling tube to be prepared is incorrect.

As said characteristic information, a tube diameter, a tube length, an existence of a cap, a cap diameter, a cap length, a cap color, an existence of a medical fluid inside a tube, and/or an existence of a label of a tube surface may be used. The automatic blood-sampling tube preparation device according to the present invention may judge whether the type of blood-sampling tube is correct on the basis of one of these characteristic information or combination of two or more information of these characteristic information.

Also, said photographing means may be arranged upstream of the label printing and pasting means in the transporting direction of the blood-sampling tube so that before the label is pasted on the blood-sampling tube, it is possible to judge whether the type of said blood-sampling tube is correct. Since the label is not pasted on the wrong blood-sampling tube, the preparation device according to the present invention is never to waste the blood-sampling tubes.

Furthermore, according to the present invention the control means may stop the transfer means if control means judges that the taken-out blood-sampling tube is incorrect, so that there is no possibility that the wrong blood-sampling tube is discharged from the automatic blood-sampling preparation device.

Also, according to the present invention the automatic blood-sampling tube preparation device may further comprise an input means by which a user inputs a user judgment result, the control means may output the judgment result via the output means by using the image and/or the sound if control means judges that the taken-out blood-sampling tube is incorrect. And then the control means may receive as the final judgment result the user judgment result judged by the user on the basis of the outputted judgment result to control each means on the basis of the final judgment result so that it is possible to make a more accurate judgment.

Furthermore, according to the present invention, when the control means judges that the taken-out blood-sampling tube is incorrect, said control means may control the label printing and pasting means so as to attach a mark which indicates that the blood-sampling tube is incorrect on the blood-sampling tube in question. Therefore, even if the taken-out blood-sampling tube is incorrect, it continues to be operated the automatic blood-sampling tube preparation device.

BRIEF DESCRIPTION OF THE DRAWINGS

FIG. 6A shows a flow chart of an embodiment of the judgment process in a judgment means 42 together with FIG. 6B.

DETAILED DESCRIPTION

Referring accompanying drawings, there will be described an embodiment of the automatic blood-sampling tube preparation device according to the present invention hereinafter.

Figure 1:
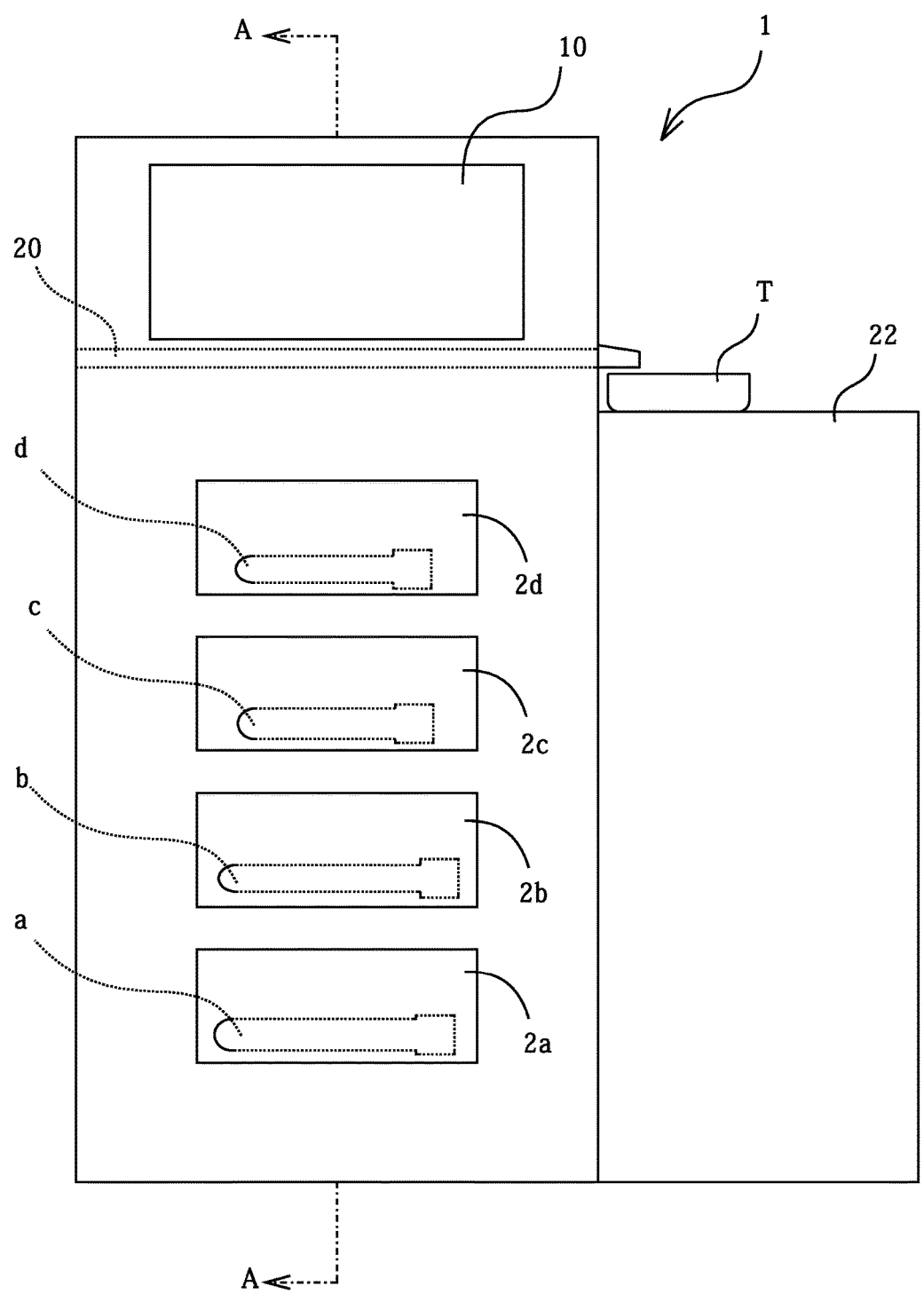
FIG. 1 is a schematic front view of an embodiment of an automatic blood-sampling tube preparation device according to the present invention.
Figure 2:
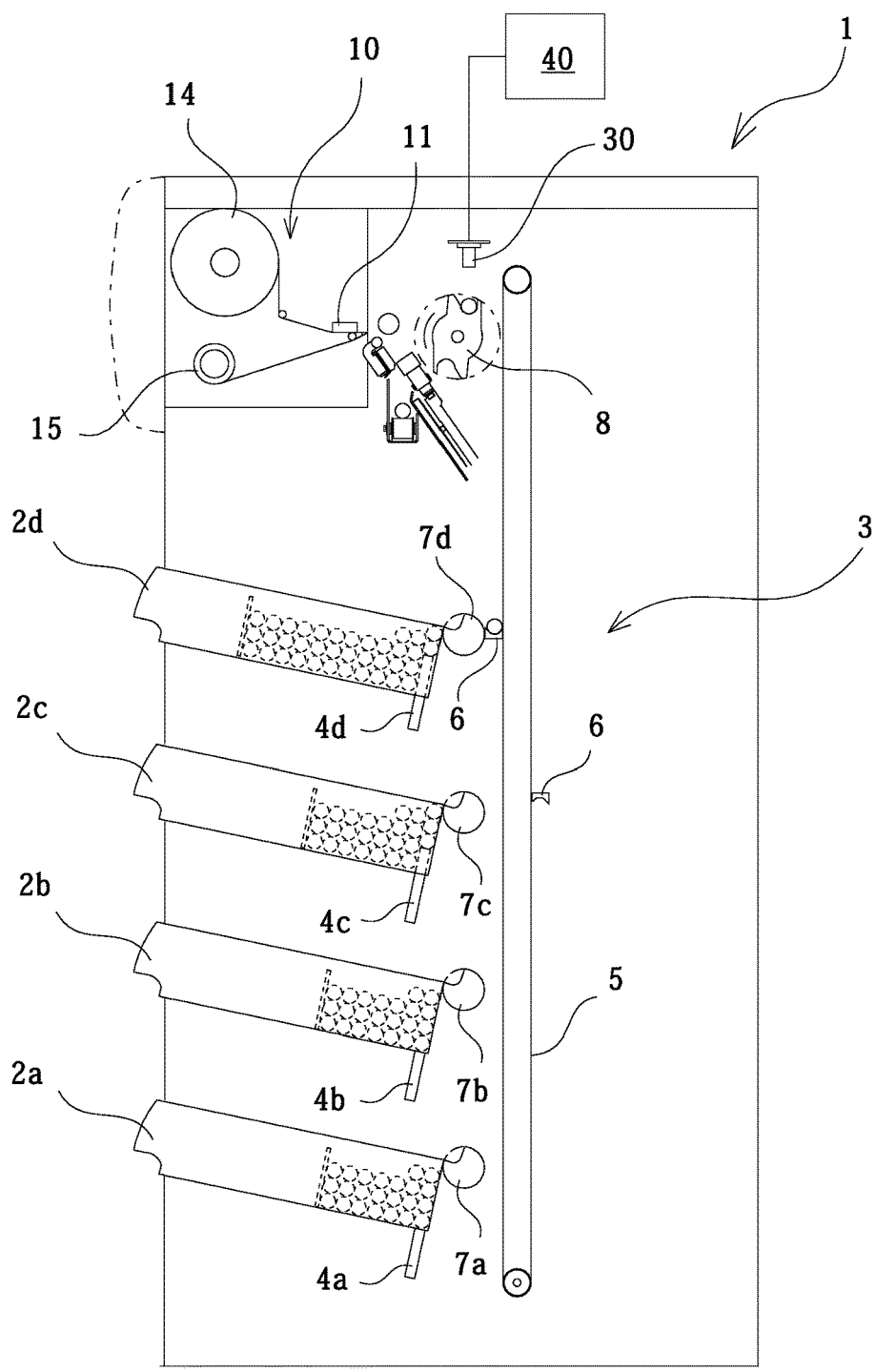
FIG. 2 is a schematic cross sectional view along the A-A line of the automatic blood-sampling tube preparation device shown in FIG. 1.
Figure 3:
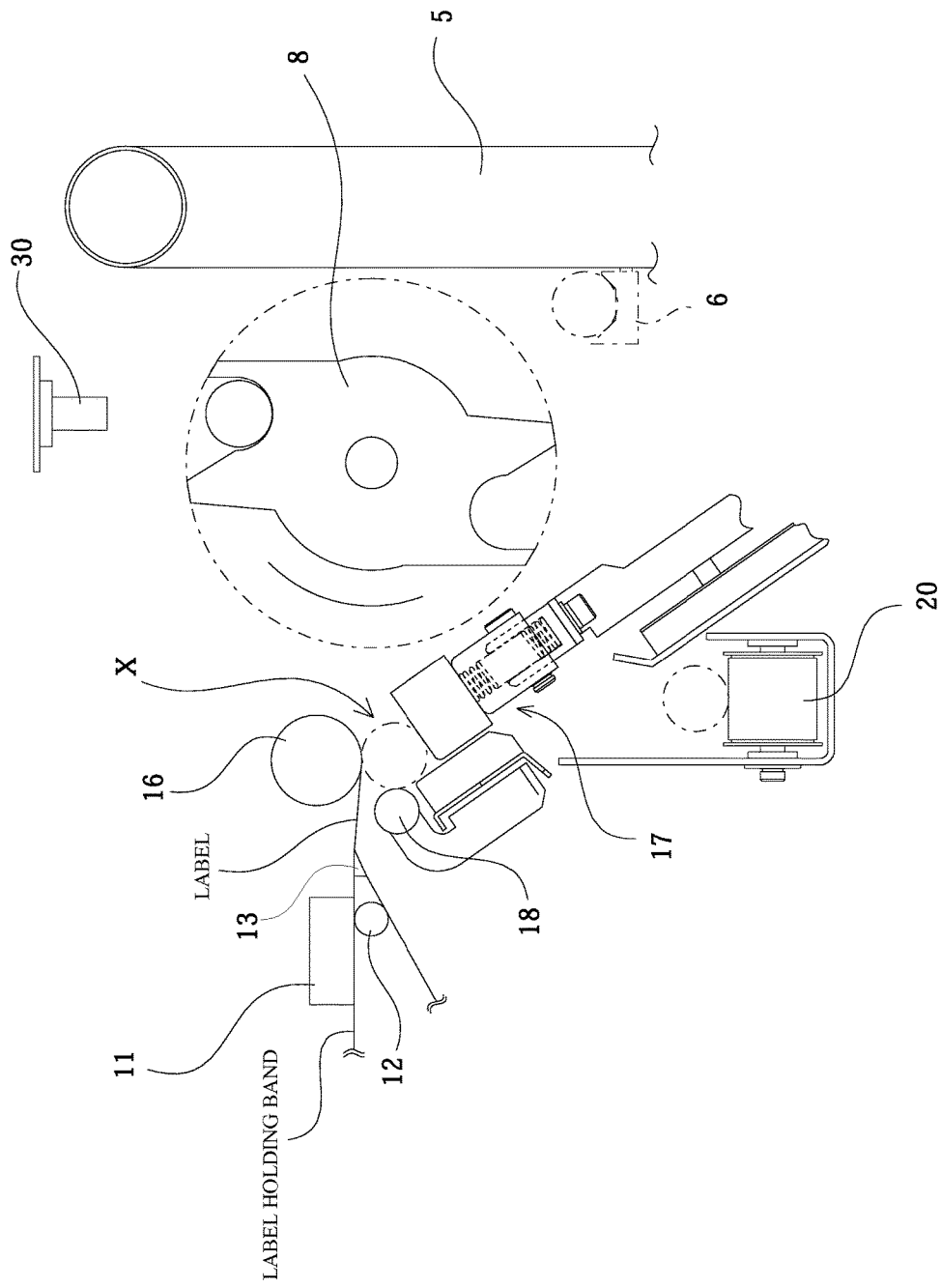
FIG. 3 is an enlarged view around a label pasting position X in the automatic blood-sampling tube preparation device shown in FIG. 1.
Figure 4:
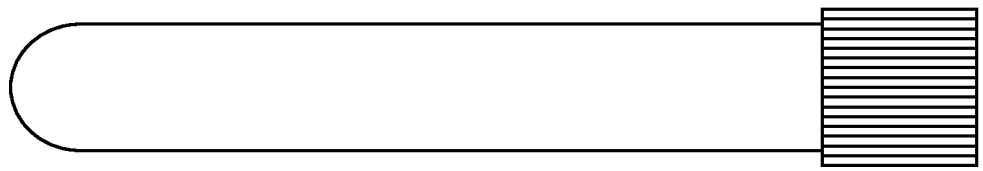
FIG. 4 shows some embodiments of the blood-sampling tubes used in the automatic blood-sampling tube preparation device in FIG. 1.
Figure 4:
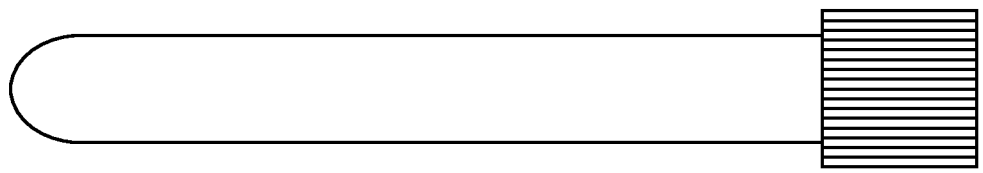
Figure 4:
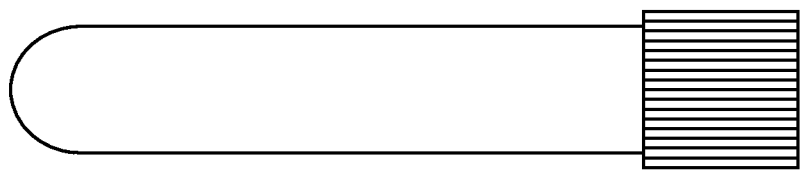
Figure 4:
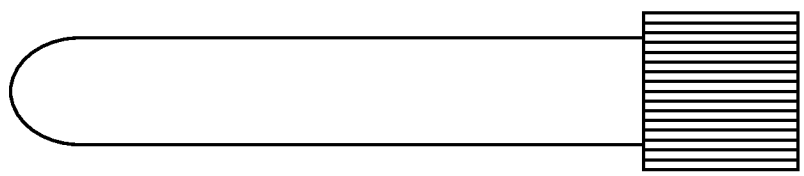

FIG. 1 is a front view schematically showing the embodiment of the automatic blood-sampling tube preparation device according to the present invention. FIG. 2 is a schematic cross sectional view along the A-A line of the automatic blood-sampling tube preparation device shown in FIG. 1. FIG. 3 is an enlarged view around the label pasting position X in the automatic blood-sampling tube preparation device shown in FIG. 1. FIG. 4 shows some embodiments of the blood-sampling tubes used in the automatic blood-sampling tube preparation device in FIG. 1.

In the drawings a numeral 1 indicates the automatic blood-sampling tube preparation device.

In this embodiment, four kinds of blood-sampling tubes a, b, c and d, of which appearances are different to each other, are used for the automatic blood-sampling tube preparation device 1. Specifically, the blood-sampling tubes a and b have same tube lengths but different tube diameters. The blood-sampling tubes c and d also have same tube lengths but different tube diameters. And the lengths of the blood-sampling tubes a and b are different from the lengths of the blood-sampling tubes c and d.

The automatic blood-sampling tube preparation device 1 includes four blood-sampling tube containing sections 2a-2d for containing bloods-sampling tubes of a same type respectively and a transferring means 3 for selectively taking out one or more blood-sampling tubes from the corresponding blood-sampling tube containing sections 2a-2d and transferring the taken-out blood-sampling tubes to a label pasting position X of a label printing and pasting means 10 after mentioned.

The transferring means 3 comprises four pushing means 4a to 4d for pushing out a blood-sampling tube from the each blood-sampling tube containing section 2a to 2d.

The transferring means 3 also comprises four first delivery means 7a-7d which receive the blood-sampling tube pushed out by the each pushing means 4a-4d and pass the received blood-sampling tube to a rack 6 provided on a transferring conveyor 5.

Said transferring conveyor 5 extends to the label printing and pasting means 10 provided on the upper portion of the automatic blood-sampling tube preparation device 1 along the blood-sampling tube containing section 2a-2d.

The transferring means 3 comprises a second delivery means 8 which receives the blood-sampling tube from the rack 6 of the transferring conveyor 5 and passes the received blood-sampling tube to the label pasting position X of the label printing and pasting means 10.

In this embodiment, the blood-sampling tubes a are contained in the blood-sampling tube containing section 2a, the blood-sampling tubes b are contained in the blood-sampling tube containing section 2b, the blood-sampling tubes c are contained in the blood-sampling tube containing section 2c, and the blood-sampling tubes d are contained in the blood-sampling tube containing section 2d.

The label printing and pasting means 10 includes a printer 11, a platen roller 12, a peeling member 13, a label holding band feed roller 14, a label holding band recovery roller 15, a pasting roller 16, a pressing means 17, and a support roller 18. The label pasting position X is defined by the pasting roller 16, the support roller 18 and the pressing means 17.

Said label printer 11 prints the examination information and/or the patient information on a label with the form of a bar code and characters based on instruction information from a doctor corresponding to the blood-sampling tube transferred to the label pasting position X so that an identification label is made.

The identification label made by the label printer 11 is sent towards between the blood-sampling tube positioned in the label pasting position X and the pasting rollers 16.

Said pressing means 17 comprises a pressing roller and a mounting. The mounting is movable back and forth so that the pressing roller mounted on the mounting is moved toward the label pasting position X when the mounting moves forth.

Before the blood-sampling tube is supplied from the second delivery means 8 to a top of the pressing roller, the mounting of the pressing means 17 is positioned in lower position where the pressing roller of the pressing means 17 is positioned away from the label pasting position X. If the blood-sampling tube is supplied from the second delivery means 8 to the top of the pressing roller, the pressing means 17 moves upwardly so that the pressing roller pushes up the blood-sampling tube and presses it against the pasting roller 16.

The position where the blood-sampling tube is pressed against the pasting roller 16 by the pressing means 17 is label pasting position X. In the label pasting position X the blood-sampling tube is supported by the pasting roller 16, the support roller 18, and the pressing means 17.

The label is pasted completely on an outer surface of the blood-sampling tube, and then the pressing means 17 is moved downwardly together with the blood-sampling tube so that the blood-sampling tube on which the label has been pasted is dropped onto a discharge conveyer 20.

The blood-sampling tube discharging conveyor 20 is extended horizontally, and discharges the blood-sampling tube with the label pasted to a tray T.

A blood-sampling tube recovery device 22 stores one or more blood-sampling tubes for one patient in the tray. After that recovery device 22 changes the tray T in which one or more blood-sampling tubes for one patient are stored for a next empty tray.

A camera 30 which constitutes the photographing means according to the present invention is provided above the said second delivery means 8.

The image data photographed by the camera 30 is sent to a control device 40.

Figure 5:
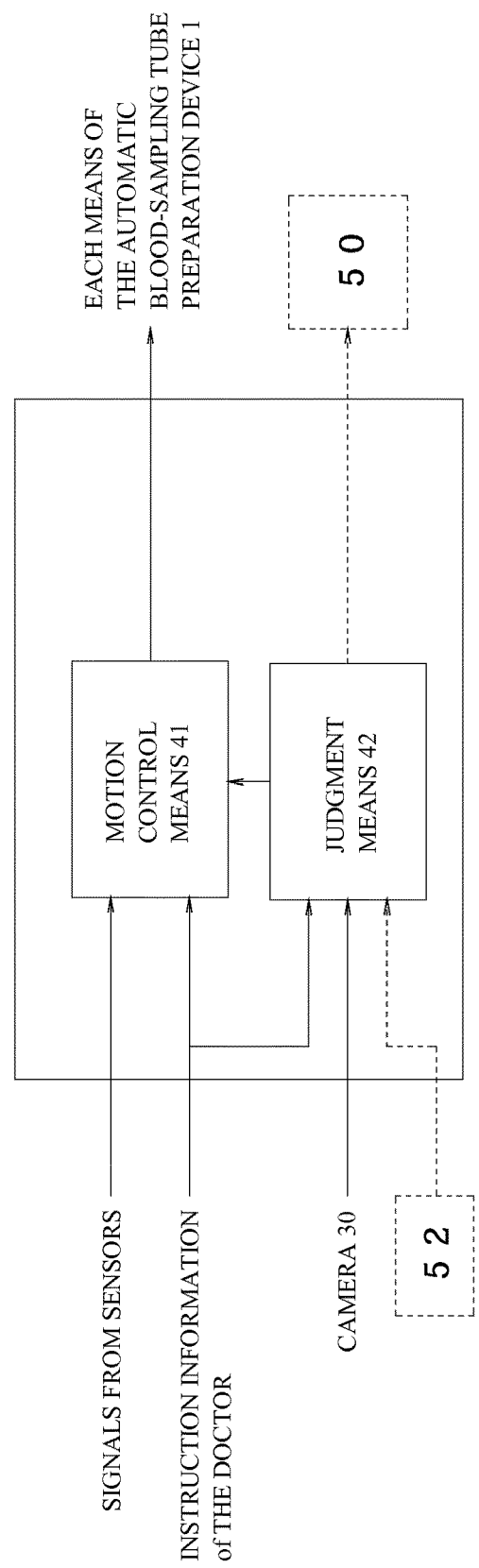
FIG. 5 is a schematic block diagram of a control device 40.

FIG. 5 is a schematic block diagram of the control device 40.

The control device 40 includes a motion control means 41 which controls operation of each above-mentioned means, and a judgment means 42 which judges the whether the blood-sampling tube which is transferred by the transferring means 3 is correct based on the image data inputted from the camera 30.

The motion control means 41 controls the motion of the transferring means 3 based on the instruction information from the doctor and the information from sensors provided in each means so that the blood-sampling tube required to the examination is taken out from the corresponding blood-sampling tube containing section and is transferred to the label printing and pasting means 10. The instruction information may include the patient information such as patient ID, a patient name, etc., and the information about the blood sampling from the patient such as a kind of and/or the number of blood-sampling tubes which are used for blood sampling. And then the motion control means 41 controls the label printing and pasting means 10 so as to print the examination information and/or the patient information on a label with the form of a bar code and characters based on the instruction information from the doctor corresponding to the blood-sampling tube transferred to the label pasting position X so that the identification label L is made. Said printed label is pasted on the outer surface of the blood-sampling tube in the label pasting position X.

Said judgment means 42 has previously memorized one or more thresholds with respect to at least one characteristic information about appearance of the blood-sampling tube.

The judgment means 42 receives an image data (namely, an appearance image of the blood-sampling tube) of the blood-sampling tube photographed by the camera 30, and extracts at least one characteristic information about the appearance of the blood-sampling tube from the image data. Then, the judgment means 42 compares the threshold with the extracted characteristic information, and specifies the type of blood-sampling tube. And the judgment means 42 judges whether the blood-sampling tube which is transferred by the transferring means 3 is corresponding to the instruction information from the doctor based on the comparison result.

The characteristic information about the appearance used for the judgment can be arbitrarily set up according to the kind of blood-sampling tube to be used. When two or more kinds of blood-sampling tubes of which only the tube lengths are different are used the tube length is used as characteristic information. Also when two or more kinds of the blood-sampling tubes, which have differences in the "the tube length" and the "the cap length" are used, the tube length and the cap length may be used as characteristic information. As characteristic information about the appearance of the blood-sampling tube usable for the judgment, for example, "the diameter of a tube", "the existence of a cap", "the diameter of a cap", "the color of a cap", "the existence of the medical fluid inside a tube", "the existence of a label of a tube surface", etc. are mentioned besides "the tube length" and "the cap length".

The judgment means 42 uses one or more characteristic information according to the type of the blood-sampling tube to be used for judgment.

In this embodiment, there are used four kinds of blood-sampling tubes of which "the tube length" and/or "the tube diameter" are different from each other. Therefore, the judgment means 42 previously memorizes the threshold with respect to "the tube length" and "the tube diameter." Also judgment means 42 extracts "the tube length" and "the tube diameter" from the image data photographed by the camera 30 as characteristic information about appearance of the tube.

Figure 6B:
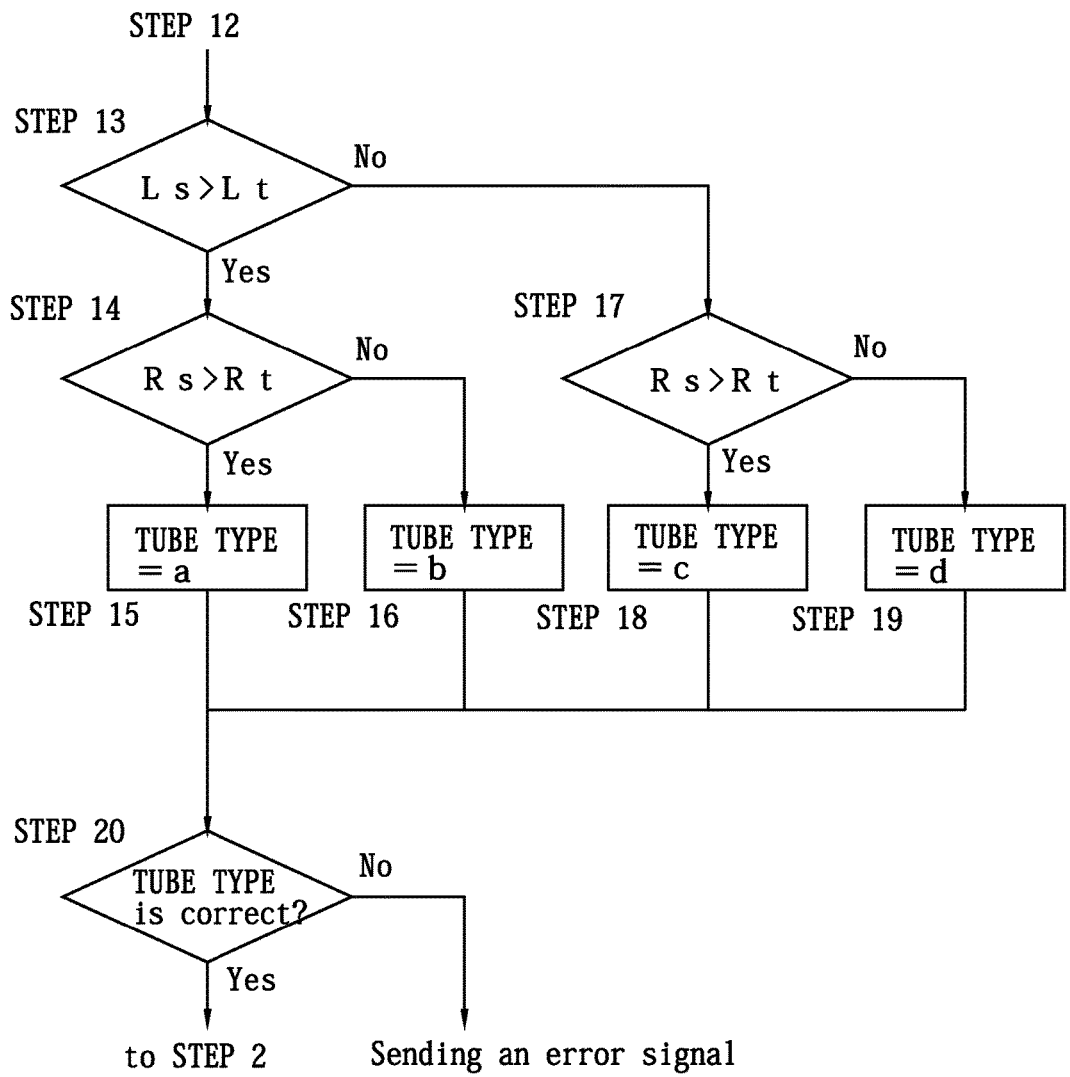
FIG. 6B shows a flow chart of an embodiment of the judgment process in the judgment means 42 together with FIG. 6A.

FIG. 6 shows a flow chart of the embodiment of the judgment process in the judgment means 42.

First, the camera 30 photographs the second delivery means 8 in the state where the blood-sampling tube is not carried. The judgment means 42 receives the image data photographed by the camera 30 as a reference image data (Step 1).

The second delivery means 8 receives the blood-sampling tube from the rack 6 of the transfer conveyor 5. Then, the second delivery means 8 carries the received blood-sampling tube to the position just under the camera 30, and stops it temporarily in this position.

In this state, the camera 30 photographs the blood-sampling tube held at the second delivery means 8, and the judgment means 42 receives that image data photographed by the camera 30 as an appearance image of the blood-sampling tube (Step 2).

The judgment means 42 performs an edge detection process using a known image processing method to the received appearance image of the blood-sampling tube (Step 3). Subsequently, the judgment means 42 performs a difference calculation process between the appearance image of the blood-sampling tube after edge detection process, and the reference image (Step 4), and the judgment means 42 performs a binarization of the difference data after the difference calculation process (Step 5).

And the judgment means 42 computes a transverse direction projection data of the blood-sampling tube by accumulating the pixel value binarized in the transverse direction to the appearance image data of the blood-sampling tube received from the camera 30 (Step 6). And then, the judgment means 42 detects an upper edge and a lower edge of the blood-sampling tube from said transverse direction projection data (Step 7), and the judgment means 42 computes "the tube diameter" which is one of the characteristic information about the appearance of the blood-sampling tube based on the upper and lower edges data. Hereinafter, it is appreciated that the "the extraction tube diameter Rs" is meant by "the computed tube diameter."

Subsequently, the judgment means 42 performs said mentioned edge detection process (Step 8), the difference calculation process (Step 9), and the binarization process (Step 10) to the received appearance image of the blood-sampling tube again. Then, the judgment means 42 computes a lengthwise direction projection data of the blood-sampling tube by accumulating the pixel value binarized in the lengthwise direction to the appearance image data of the blood-sampling tube received from the camera 30 (Step 11). And the judgment means 42 detects a right edge and a left edge of the blood-sampling tube from the lengthwise direction projection data (Step 12), and the judgment means 42 computes "the tube length" which is one of the characteristic information about the appearance of the blood-sampling tube. Hereinafter, it is appreciated that "the extraction tube length Ls" is meant by "the computed tube length."

The judgment means 42 compares "the extraction tube diameter Rs" and "the extraction tube length Ls" which are the characteristic information about the appearance of the blood-sampling tube with the thresholds (the tube diameter threshold Rt and the tube length threshold Lt) with respect to "the tube diameter" and "the tube length" previously stored. And the judgment means 42 performs a tube type specific process in which the kind of the blood-sampling tube is specified, based on said comparison result.

In this embodiment, for example, the blood-sampling tube a has 100 mm of the tube length and 15.6 mm of the tube diameter, the blood-sampling tube b has 100 mm of the tube length and 13.2 mm of the tube diameter, the blood-sampling tube c has 78 mm of the tube length and 15.6 mm of the tube diameter, and the blood-sampling tube d has 78 mm of the tube length and 13.2 mm of the tube diameter.

And the tube length threshold Lt memorized by the judgment means 42 is 90 mm, and the tube diameter threshold Rt memorized by the judgment means 42 is 15 mm.

Hereinafter, said tube type specific process will be particularly explained. First, judgment means 42 judges whether the extraction tube length Ls is longer than the threshold Lt of tube length, i.e. 90 mm (Step 13).

In case that the extraction tube length Ls is longer than the tube length threshold Lt in the Step 13, the judgment means 42 judges whether the extraction tube diameter Rs is larger than the threshold Rt of tube diameter, i.e. 15 mm (Step 14).

In case that the extraction tube diameter Rs is larger than the tube diameter threshold Rt in the Step 14, the blood-sampling tube photographed by the camera 30 has the tube length which is longer than 90 mm and the tube diameter which is larger than 15 mm and therefore the type of the blood-sampling tube is the blood-sampling tube a. In this case, therefore, the judgment means 42 specifies that "the tube type" of the blood-sampling tube is the blood-sampling tube a (Step 15).

In case that the extraction tube diameter Rs is smaller than the tube diameter threshold Rt in the Step 14, the blood-sampling tube photographed by the camera 30 has the tube length which is longer than 90 mm and the tube diameter which is smaller than 15 mm and therefore the type of the blood-sampling tube is the blood-sampling tube b. In this case, therefore, the judgment means 42 specifies that "the tube type" of the blood-sampling tube is the blood-sampling tube b (Step 16).

In case that the extraction tube length Ls is shorter than the tube length threshold Lt in the Step 13, the judgment means 42 judges whether the extraction tube diameter Rs is larger than the tube diameter threshold Rt, i.e. 15 mm (Step 17).

In case that the extraction tube diameter Rs is larger than the tube diameter threshold Rt in the Step 17, the blood-sampling tube photographed by the camera 30 has the tube length which is shorter than 90 mm and the tube diameter which is larger than 15 mm and therefore the type of the blood-sampling tube is the blood-sampling tube c. In this case, therefore, the judgment means 42 specifies that "the tube type" of the blood-sampling tube is the blood-sampling tube c (Step 18).

In case that the extraction tube diameter Rs is smaller than the tube diameter threshold Rt in the Step 17, the blood-sampling tube photographed by the camera 30 has the tube length which is shorter than 90 mm and the tube diameter which is smaller than 15 mm and therefore the type of the blood-sampling tube is the blood-sampling tube d. In this case, therefore, the judgment means 42 specifies that "the tube type" of the blood-sampling tube is the blood-sampling tube d (Step 19).

After that the judgment means 42 judges whether the tube type of the blood-sampling tube photographed by the camera 30 is included in the instruction information of the doctor (Step 20). In case that the tube type of the blood-sampling tube is correct, the motion control means 41 resumes the operation of the second delivery means 8 to transfer the blood-sampling tube toward the label pasting position X. The judgment means 42 waits to receive a next image data of the following blood-sampling tube from the camera 30, and if the judgment means 42 receives the next image data, it will start processing from processing of Step 2 again. In case that the tube type of the blood-sampling tube isn't correct, the judgment means 42 sends an error signal to the motion control means 41 to stop the each means.

Therefore the user can remove the undesirable blood-sampling tube from the device, or can change it to the desirable blood sampling tube.

As described above, in the automatic blood-sampling tube preparation device according to this embodiment, the appearance of the blood-sampling tube taken out from the blood-sampling tube containing section is photographed by the camera 30. Then the judgment means 42 extracts the characteristic information from the photographed appearance image of the blood-sampling tube, compares the extracted characteristic information with the threshold previously stored with respect to the characteristic information, and specifies the kind of the blood-sampling tube based on the comparison result. The judgment means 42 judges whether the tube type of the blood-sampling tube photographed by the camera 30 is correct based on the instruction information from the doctor, and if the tube type of the blood-sampling tube isn't correct, the judgment means 42 sends the error signal to the motion control means 41 to stop the each means. Therefore, in the automatic blood-sampling tube preparation device according to the present embodiment, the undesirable blood-sampling tube is not discharged.

In the automatic blood-sampling tube preparation device according to this embodiment, the camera 30 is arranged upstream of the label printing and pasting means 10 in the transferring direction of the blood-sampling tube. Before carrying out the label printing and pasting process to the blood-sampling tube by the label printing and pasting means 10, the correct and incorrect judgment of the blood-sampling tube can be made so that a label is not pasted on the incorrect blood-sampling tube and the blood-sampling tube is not made useless.

In the above-mentioned embodiment, if the blood-sampling tube photographed by the camera 30 is incorrect, the judgment means 42 sends the error signal to the motion control means 41 to stop the each means. However, the process after the judgment by the judgment means 42 is not limited to this embodiment.

For example a monitor 50 and an input means 52 may be provided in the automatic blood-sampling tube preparation. In this case, if the blood-sampling tube photographed by the camera 30 is incorrect, the image of the blood-sampling tube photographed by the camera 30 may be displayed on the monitor 50. And a user may visually inspect the displayed image and judge whether the type of the blood-sampling tube is correct, and input the result of his judgment via the input means 52. In this case, the judgment means 42 may be constituted so that it sends to the error signal to stop the each means based on the user judgment inputted by the user via the input means 52. Alternatively, when the device is already suspended, the judgment means 42 may be constituted so that the device may be again operated based on the final user judgment.

Also the automatic blood-sampling tube preparation device according to the present invention may be constituted as follows. For example, even if the blood-sampling tube photographed by the camera 30 is incorrect the judgment means 42 does stops the each means of the preparation device, the judgment means 42 may only send to an error signal to the label printing and pasting device 10 so that the label printing and pasting device 10 prints an error information on a label and pastes it on the surface of the incorrect blood-sampling tube.

Furthermore, the judgment means 43 of the automatic blood-sampling tube preparation device according to the present invention may be constituted as follows. The discharge conveyor 20 may be constituted so that if the blood-sampling tube photographed by the camera 30 isn't correct, the undesirable blood-sampling tube is discharged by the discharge conveyor 20 to eliminate the undesirable tube from the usual processing route.

In the above-mentioned embodiment, the each blood-sampling tube containing section is constituted so that one or more blood-sampling tubes may be contained in the containing section in the state where they were horizontally laid and two or more containing sections are superposed in the preparation device. However, the arrangement of the automatic blood-sampling tube preparation device according to the present invention is not limited to this embodiment. For example, the blood-sampling tube containing section may comprise a rack in which one or more blood-sampling tubes are held in a standing condition. In this case, the transferring means may comprise a robot arm which operates with the X-Y axis established on said rack.

What is claimed is:

1. An automatic blood-sampling tube preparation device comprising
   at least two blood-sampling tube containing sections, each section being intended to contain blood-sampling tubes of a same type,
   a transferring device for selectively taking out a blood-sampling tube required to an examination of a patient according to an instruction information indicated by a doctor from the blood-sampling tube containing section and transferring the taken-out blood-sampling tube to a label pasting position,
   a label printing and pasting device for printing an information of the patient on a label and pasting the printed label on the blood-sampling tube positioned in the label pasting position, and
   a control device for controlling operations of each device
   wherein
   the automatic blood-sampling tube preparation device further comprises a photographing device for photographing an appearance of the blood-sampling tube taken out from the blood-sampling tube containing section,
   said photographing device is arranged upstream of the label printing and pasting device in the transporting direction of the blood-sampling tube, and
   said control device is arranged
   to have a threshold with respect to at least one characteristic information previously extracted from an appearance of a blood-sampling tube,
   to extract the characteristic information from the appearance image photographed by the photographing device,
   to specify the type of the blood-sampling tube taken out from the blood-sampling tube containing section on the basis of the threshold and the extracted characteristic information, and
   to judge whether the blood-sampling tube corresponds to the instruction information from the doctor before transferring the taken-out blood-sampling tube to a label pasting position.

2. The automatic blood-sampling tube preparation device according to claim 1, wherein
   said characteristic information includes at least one of a tube diameter, a tube length, an existence of a cap, a cap diameter, a cap length, a cap color, an existence of a medical fluid inside a tube, and an existence of a label of a tube surface.

3. The automatic blood-sampling tube preparation device according to claim 1, wherein
   the control device stops the transfer device if the control device judges that the taken-out blood-sampling tube is incorrect.

4. The automatic blood-sampling tube preparation device according to claim 1, wherein
   the automatic blood-sampling tube preparation device further comprises an output device for outputting the judgment result by the control device to a user, and
   the control device outputs the judgment result via the output device by using an image and/or a sound if the blood-sampling tube taken out from the blood-sampling tube containing section is incorrect.

5. The automatic blood-sampling tube preparation device according to claim 4, wherein
   the automatic blood-sampling tube preparation device further comprises an input device by which a user inputs a user judgment result,
   the control device outputs the judgment result via the output device by using the image and/or the sound if the control device judges that the taken-out blood-sampling tube is incorrect, and then
   the control device receives as the final judgment result the user judgment result judged by the user on the basis of the outputted judgment result via the input device to control each device on the basis of the final judgment result.

6. The automatic blood-sampling tube preparation device according to claim 1, wherein
   when the control device judges that the taken-out blood-sampling tube is incorrect, said control device controls the label printing and pasting device so as to attach a mark which indicates that the blood-sampling tube is incorrect on the blood-sampling tube in question.

7. The automatic blood-sampling tube preparation device according to claim 2, wherein
   the control device stops the transfer device if the control device judges that the taken-out blood-sampling tube is incorrect.

8. The automatic blood-sampling tube preparation device according to claim 2, wherein
   the automatic blood-sampling tube preparation device further comprises an output device for outputting the judgment result by the control device to a user, and
   the control device outputs the judgment result via the output device by using an image and/or a sound if the blood-sampling tube taken out from the blood-sampling tube containing section is incorrect.

9. The automatic blood-sampling tube preparation device according to claim 8, wherein
   the automatic blood-sampling tube preparation device further comprises an input device by which a user inputs a user judgment result,
   the control device outputs the judgment result via the output device by using the image and/or the sound if the control device judges that the taken-out blood-sampling tube is incorrect, and then
   the control device receives as the final judgment result the user judgment result judged by the user on the basis of the outputted judgment result via the input device to control each device on the basis of the final judgment result.

10. The automatic blood-sampling tube preparation device according to claim 2, wherein
   when the control device judges that the taken-out blood-sampling tube is incorrect, said control device controls the label printing and pasting device so as to attach a mark which indicates that the blood-sampling tube is incorrect on the blood-sampling tube in question.

* * * * *